United States Patent
Torstensen et al.

(10) Patent No.: US 8,506,537 B2
(45) Date of Patent: Aug. 13, 2013

(54) SEALING DEVICE

(75) Inventors: Jan Torstensen, Virum (DK); Allan Tanghoj, Kokkedal (DK)

(73) Assignee: Coloplast A/S, Humlebaek (DK)

( * ) Notice: Subject to any disclaimer, the term of this patent is extended or adjusted under 35 U.S.C. 154(b) by 1351 days.

(21) Appl. No.: 10/490,854

(22) PCT Filed: Oct. 14, 2002

(86) PCT No.: PCT/DK02/00688
§ 371 (c)(1),
(2), (4) Date: Mar. 26, 2004

(87) PCT Pub. No.: WO03/030967
PCT Pub. Date: Apr. 17, 2003

(65) Prior Publication Data
US 2004/0267198 A1 Dec. 30, 2004

(30) Foreign Application Priority Data

Oct. 12, 2001 (DK) ................................. 2001 01510
Dec. 21, 2001 (DK) ................................. 2001 01946

(51) Int. Cl.
*A61M 5/00* (2006.01)
(52) U.S. Cl.
USPC ........ 604/264; 604/93.01; 604/275; 604/278; 604/337; 604/355; 604/513; 600/29; 600/32; 600/30; 600/31; 600/1; 128/885; 128/887; 128/834; 428/317.9

(58) Field of Classification Search
USPC .............. 604/93.01, 264, 275, 278, 337, 355, 604/513; 600/29, 32, 1, 30, 31; 128/885, 128/887, DIG. 25, 834; 428/317.9
See application file for complete search history.

(56) References Cited

U.S. PATENT DOCUMENTS

| | | | | |
|---|---|---|---|---|
| 2,324,520 A | * | 7/1943 | Lamson | 600/32 |
| 2,510,766 A | * | 6/1950 | Surface | 600/32 |
| 2,564,399 A | * | 8/1951 | Franken | 600/32 |
| 2,631,586 A | | 3/1953 | Reilly | |
| 3,253,594 A | * | 5/1966 | Matthews et al. | 604/103.03 |
| 3,344,791 A | | 10/1967 | Foderick | |
| 3,447,533 A | * | 6/1969 | Spicer | 600/32 |
| 3,459,175 A | | 8/1969 | Miller | |
| 3,721,229 A | * | 3/1973 | Panzer | 600/435 |
| 3,731,682 A | | 5/1973 | Fielding | |
| 3,765,413 A | * | 10/1973 | Lepar | 604/176 |
| 3,802,418 A | * | 4/1974 | Clayton | 600/562 |
| 4,117,847 A | * | 10/1978 | Clayton | 604/97.01 |

(Continued)

FOREIGN PATENT DOCUMENTS

| | | |
|---|---|---|
| CA | 2438320 | 8/2002 |
| CA | 2322526 | 7/2005 |

(Continued)

*Primary Examiner* — Nicholas Lucchesi
*Assistant Examiner* — Scott Medway
(74) *Attorney, Agent, or Firm* — Coloplast Corp., Coloplast A/S; Nick Bauman

(57) ABSTRACT

Sealing device for sealing externally debouching, natural or artificial body canals of animals or human beings, the device enabling liquid tight sealing against the inner wall of the bowel system of the animal or human being, the device further being made from a resilient material. The device is soft and resilient and may thus not trigger the analreflex, but is still able to provide a fluid-tight seal.

10 Claims, 3 Drawing Sheets

(56) References Cited

U.S. PATENT DOCUMENTS

| | | | | |
|---|---|---|---|---|
| 4,241,735 A | * | 12/1980 | Chernov | 606/192 |
| 4,344,434 A | * | 8/1982 | Robertson | 604/334 |
| 4,693,236 A | * | 9/1987 | Leprevost | 600/32 |
| 4,772,274 A | | 9/1988 | Lukacs | |
| 4,781,176 A | * | 11/1988 | Ravo | 600/30 |
| 4,784,654 A | * | 11/1988 | Beecher | 604/329 |
| 4,922,928 A | * | 5/1990 | Burnhill | 128/832 |
| 4,981,465 A | | 1/1991 | Ballan et al. | |
| 5,312,343 A | | 5/1994 | Krog et al. | |
| 5,562,599 A | | 10/1996 | Beyschlag | |
| 5,800,338 A | | 9/1998 | Kollerup et al. | |
| 5,887,593 A | * | 3/1999 | Levius | 128/885 |
| 6,090,038 A | * | 7/2000 | Zunker et al. | 600/29 |
| 6,096,057 A | * | 8/2000 | Klingenstein | 606/197 |
| 6,482,214 B1 | * | 11/2002 | Sidor et al. | 606/151 |
| 6,558,370 B2 | * | 5/2003 | Moser | 604/317 |
| 6,723,108 B1 | * | 4/2004 | Jones et al. | 606/151 |
| 2003/0125603 A1 | * | 7/2003 | Zunker et al. | 600/29 |

FOREIGN PATENT DOCUMENTS

| | | |
|---|---|---|
| DK | 148054 B | 12/1980 |
| EP | 0 759 734 | 3/1997 |
| HU | 219990 | 5/1998 |
| HU | 1441 U | 12/1998 |
| JP | S39-9888 | 4/1964 |
| JP | S55-108358 | 8/1980 |
| JP | S56-67796 | 5/1981 |
| JP | S56-108276 | 7/1981 |
| JP | S60-201324 | 12/1985 |
| JP | H08-164162 | 6/1996 |
| JP | H09-511920 | 12/1997 |
| NL | 8902835 | 6/1991 |
| WO | WO 95/28138 | 10/1995 |
| WO | WO 98/23312 | 6/1998 |

* cited by examiner

SEALING DEVICE

This is a nationalization of PCT/DK02/00688 filed Oct. 14, 2002 and published in English and a continuing application of U.S. Ser. No. 10/058,375, filed Jan. 30, 2002.

BACKGROUND OF THE INVENTION

1. Field of the Invention

The present invention relates to a sealing device for sealing externally debouching, natural or artificial body canals of animals or human beings, the device enabling liquid tight sealing against the inner wall of the bowel system of the animal or human being, especially when performing irrigation through a natural or artificial body opening of the animal or human being. The invention further relates to the use of such a device.

The device is especially suitable as a sealing member incorporated with a disposable trans-anal or trans-stomal irrigation probe.

Faecal continence can be defined as the ability to control defecation, to be able to distinguish flatus from loose respectively formed faeces or to be able to maintain faecal continence even during sleep without use of external aids. In the bowel system the nerves and muscles of the colon, rectum and anus function together in a closely co-ordinated manner in order to maintain continence. In case of any malfunction e.g. if a person is suffering from some kind of defect in the control of the bowel, this person will very likely be incontinent. The defects may e.g. occur as result of a spinal cord injury, multiple sclerosis (MS), tumours or metastases, diabetes, spina bifida or ideopatic constipation.

In addition to surgical treatment of faecal incontinence, medication and regulating nutrition, meal times and defecation habits, enemas or irrigation are some of the treatments that have been practised for long time. Enemas or irrigation may also be used by completely healthy people if they for some reason want a colonic lavage.

2. Description of the Related Art

For these purposes several devices have been proposed in the past. In addition to devices especially for use of performing irrigation for treatment of incontinence, other similar devices have been proposed for irrigation, e.g. products developed for administration of barium sulphate enema or the like as part of a radiological examination.

One example of a prior art device is disclosed in U.S. Pat. No. 3,459,175. The device includes an inflatable balloon for giving enemata. The balloon is located on the probe for introduction of irrigation liquid, and the balloon is to be inflated when positioned in the rectum of the patient close to the anal opening. The ballooned annular element thereby blocks for undesired flow from the bowel through anus.

However, existing enemata probe sealings of the type provided with inflatable balloons inherently possess a number of disadvantages.

To ensure a sufficiently tight sealing to be obtained when placed in the bowel system, the balloon is often inflated to a greater size than necessary thereby exerting an excessive pressure on the bowel wall and even on a larger surface than intended or necessary. Furthermore, all known products on the market have relatively hard and incompressible balloons. This is likely to induce refectory contraction of the muscles in the bowel and the lower part of colon, resulting in the enemata probe being forced out through the anal opening. Further to the unpleasant leakage, as a result of such premature displacement of the probe with the balloon still being inflated may cause serious injury to the fragile wall of rectum. Also, when expanding in axial direction the balloon may be brought to cover the openings of the probe, thus stopping the intended flow of liquid into the bowel system. Furthermore, there is a risk that a balloon may be overfilled and may result in a rupture of the balloon. Such a situation may likewise cause damage of the fragile wall of the rectum, leakage of the liquid filled content of the colon sigmoideum and rectum and stress of the patient. Also, the balloon may leak which will let the air of the balloon leak out. As a result of this, the device suddenly may fall out of the rectum followed by an unintended leakage of faecal matter. As the users of enemata probes may have no sensory function in the rectum they may not themselves immediately register if the device is falling out. Finally, balloons used in these devices are often made from latex. This may cause problems for patients and others suffering from latex allergy.

When having to perform irrigation on small children another problem may arise as the devices commercially available today are rather large, they therefore seem relatively scaring both for the small children and for their parents.

Another disadvantage in connection with the mentioned products are that they are too expensive to be used as disposable products. According to specialists these products are used several times for the same patient, while being cleaned in-between uses. Apart from being time consuming due to necessary cleaning steps it will be understood that the risk of contaminating the environment during storage of the product in between each use and the risk of infecting the user is much bigger than compared to the risk when using disposable products.

A disposable kit for trans-anal irrigation is described in WO 98/23312. The kit comprises a container for irrigation media and is connected to a catheter or probe through which the enemata liquid is administered into the bowel system. The probe is provided with a fixation member intended to ensure fixation of the probe inside the bowel system during inlet of the enemata liquid. The fixation member is made from a compressible material such as a foam or a moulded elastic material. The fixation member is provided in a compressed state and surrounded by a PVA film which will dissolve when getting into contact with humidity. The fixation member is as an example made of a polyurethane and has an open structure to allow for air passing through during irrigation. Using a foam material secures a lenient contact between the bowel wall and fixation member of the probe, and the open structure favourably enhances compressibility of the fixation member but has proved to imply the disadvantage of permeability for fluids during irrigation leading to undesired leakage of irrigation media and liquid bowel contents.

It is an object of the invention to provide a soft and compressible sealing device for providing liquid tight sealing properties in order to overcome the above mentioned disadvantages of sealing devices and avoiding leakage, especially avoiding triggering of the analreflex thus expulsing the device.

SUMMARY OF THE INVENTION

The present invention reveals a device for providing liquid tight sealing while avoiding the above mentioned disadvantages.

According to the invention a sealing device is provided, especially a device for sealing externally debouching, natural or artificial body canals of animals or human beings. The device is made from a resilient material e.g. a compressible foam, e.g. closed or open celled, or may be in the form of a soft and resilient balloon and can optionally be integrated with or include a sealing element. The device may have a maximum compression force of less than 4 N, more preferred between 3.5-0.2 N, more preferred between 3.0-0.25 N and most preferred between 2.0-0.25 rendering the device resilient enough for not triggering the anal-reflex or to cause damage to the colon, such as pressure ulcers.

The invention further relates to the use of a sealing device as a sealing plug providing faecal continence of a body opening. When further incorporated with a probe for administering liquids into the bowel system, use of the device provides security against leakage when performing irrigation through natural or artificial body canals of animals or human beings.

BRIEF DESCRIPTION OF THE DRAWINGS

The invention is disclosed in further detail with reference to the drawings in which.

DETAILED DESCRIPTION OF THE PRESENT INVENTION

Figure 1:
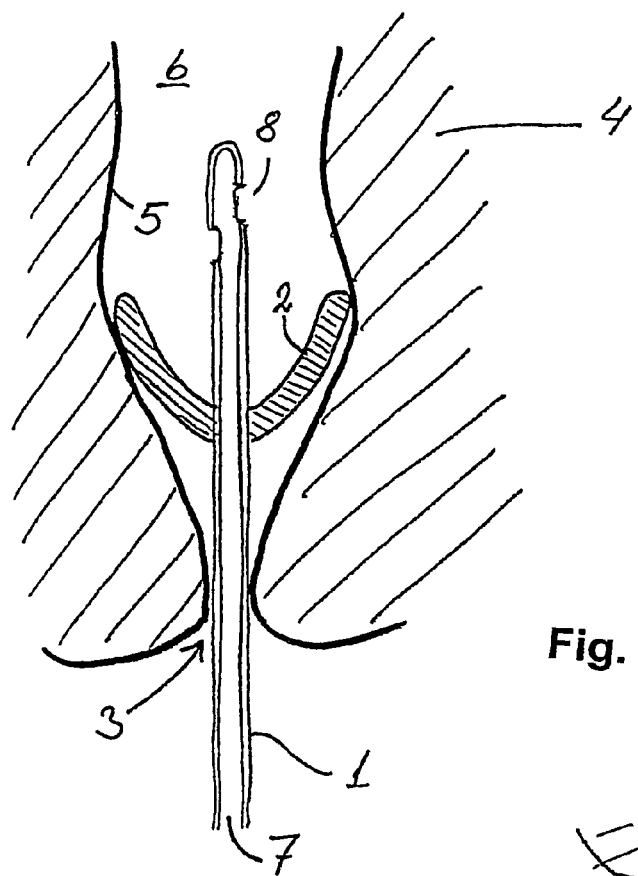
FIG. 1 illustrates a sealing device according to the invention incorporated with a probe for administration of enemata liquid and placed in the bowel system close to the anal opening of a human being.

The device can have the form and purpose of a plug, or it can be an integrated part of an instrument for use in the bowel system e.g. an instrument such as a probe for administering liquid into the bowel system. In order to ease insertion of the probe a small diameter thereof is preferred as is a small total diameter of the probe surrounded with a compressed sealing element. This will provide a probe, which is easily insertable and simple to use. In use, the cells of the sealing device made from open celled foam will tend to take up liquid from the bowel content or from the administered liquid and thereby expand. In case of using a soft and resilient balloon it is inflated after insertion. In both cases use of the device minimises the risk of inducing plug- or probe-ejecting contractions in the bowel system as the pressure exerted by the device, being a swelled type or not, against the wall of the bowel is low because the body of the sealing element is far more compliant as compared to known sealing devices.

The present invention relates to a sealing device for sealing externally debouching, natural or artificial body canals of animals or human beings, the device enabling liquid tight sealing against the inner wall of the bowel system of the animal or human being, the device further being made from a resilient material, wherein said device has a maximum compression force of less than 4 Newton.

The softness of the device of the invention is obtained by the choice of material or the physical conformation of the device or a combination of these features.

The device may comprise a sealing element.

In a preferred embodiment of the invention the sealing element comprises a foam.

A substantially dome-shaped curvature of the device may even enhance its compliability with the wall of the bowel. It is understood that a more or less pronounced inclination of the device can be chosen to optimise the sealing effect, as can the radial size of the device. Furthermore, a number of alternative shapes of sealing devices are suggested in WO 98/23312. In order to obtain a sealing device which in compressed state has as small a radial extension as possible, a thin walled device is preferred, but also more voluminous shapes of the sealing device may be relevant, especially when the sealing element is made from very compressible materials. Finally, a collar shaped termination providing a curvature somewhat deviating from the curvature of the body part of the device may be desirable and can even bring about a better sealing effect against the bowel wall.

Further, the soft and compliant feature of the sealing element is mainly provided by the nature and shape of the material it is made from. A sealing device made from open celled foam provides the device with a desired softness and conformability. At the same time the foam is sufficiently compressible to enable the device to be provided for use in a—in order to ease insertion—desirable small and pleasant compressed shape. Examples of materials for such open celled foams are PU, silicone, PVC and PE. In a preferred embodiment of the invention the foam is polyurethane (PU). However, the probe can be made from a range of materials and matching production methods. Examples of materials can be a TPE, SEB, SEBS, such as Kraton™, various PE, PU foams based on PU or PE or other materials as Silicone, Latex or synthetic rubber. Accordingly production methods can be e.g. die casting or mould casting or punching.

The device can be provided for use in a compressed state as described above being wrapped in a thin film which dissolves when brought into contact with e.g. bodily humidity i.e. when being placed inside the bowel system whereby expansion of the device is enabled. An example of material for such a thin and dissolvable film is PVA.

Alternatively the device is provided in a non-compressed state. Due to the soft and compliant structure of the sealing element the dome-like shape of the sealing element can easily be inserted. Especially when the sealing device forms part of a probe for insertion through anus, capability of the device to invert during insertion eases the insertion process and can render the thin dissolvable film for wrapping a the sealing element in compressed form superfluous. The device can be provided for insertion in a configuration ready for insertion or in opposite configuration, in which case the sealing device is suitably inverted prior to insertion.

By choosing a more or less curved profile of the outer surface of the device, i.e. the surface facing in use a natural or artificial opening to the bowel system, the person skilled in the art can optimise the capability of the device to be inverted back and forth at desired phases during use of the device. Alternative curvatures of the radial curve close to the centre-line of the sealing element can provide for different capabilities to inversion of the sealing element. Adjusting the thickness of material may further optimise the desired qualities of the device.

Providing the sealing element with a liquid tight feature may be obtained by incorporating into the sealing device a liquid tight foil or layer which prevents passage of bowel or irrigation liquids through the sealing device. This foil or layer may form the surface on one or both sides of the device, e.g. on the inner surface of the device, facing in use the content of the bowel system, or e.g. the outer surface of the device, facing in use a natural or artificial opening to the bowel system.

When the foil or layer form the inner surface of the sealing device, sealing properties of smooth character provided by the compressible material of the device can become fully exploited. On the other hand, when provided as the outer surface of the sealing device facing the bodily opening of the user, removal of the sealing device may become easier due to relatively smooth surface properties provided by the foil or layer.

In one embodiment of the invention the foil or layer may be embedded between two layers of compressible material inside the device, whereby an increased anchoring of the compressible material is obtained. This may be desirable when the compressible material chosen is of relative incoherent nature. Examples of materials for such foils or layers are e.g. plastics or hydrophobic non-wovens made from materials such as PU, silicone, TPE, latex or polyolefins.

Providing the sealing element with the liquid tight feature can also be obtained by making use of a foam possessing hydrophobic features. Hydrophobicity is obtainable as an inherent feature of the foam itself. Examples of such hydrophobic foams are foams based on PU, Silicone or PVC. A foam being sufficiently hydrophobic is alternatively obtainable by incorporating a hydrophobic agent into the foam during production or by treating the foam with a hydrophobic agent. Applicable hydrophobicity is obtainable by combining strength of hydrophobicity of material or agent with a sufficiently small cell size of the foam. In order to describe a foam material capable of substantially withstanding liquid pressure exerted thereon by liquid or solid contents in the bowel system, combinations of such foam and hydrophobic agent combinations are many. They may e.g. be combinations of foams chosen from the above mentioned foams and hydrophobic agents like silicone surfactants, various soaps or other surface reactants which increase the surface tension of the foam.

It is to be understood that the device can be made from several adjacent layers of e.g. foam or other suitable material of which at least one layer needs to provide the liquid tight properties to the device. Providing the sealing element with a liquid tight feature can further be obtained by incorporating super-absorbent particles in the foam. One preferred liquid absorbent material is sodium polyacrylate. Alternative absorbents can be chosen from a group comprising inorganic materials, such as gels, or organic compounds, such as a cross linked polymer, or alginates, reticular carboxymethylcelluloses, grafted starches, natural or modified polysaccharides or synthetic derivatives of acrylamides, acrylonitriles or polyacrylates. When being brought into contact with liquids from the bowel system or from administered irrigation or enemata fluids, the super-absorbent particles will swell and expand, thereby closing the cells of the foam to provide a liquid tight barrier. This phenomenon is known to be an undesirable consequence in relation to the use of super-absorbents in the technical field of absorbing articles, where problems arise when so-called gel-blocking occurs in upper layers of absorbing articles (pads, nappies etc.) as the intended distribution of liquid throughout the product is thereby inhibited.

A device according to the invention can be made from several layers of which at least one need to provide the device with the liquid tight quality arising from one or more of the above mentioned ways of providing a such quality.

To ease removal of the device after use it can preferably be provided with an anchored string or similar separate withdrawal means of types known in the art. This especially counts for plug type devices and a number ways of how to anchor such string or similar withdrawal means is described in European patent number EP 0759734 B1. When forming part of a probe the means for withdrawal of the device is advantageously provided by the probe itself.

In one embodiment of the invention the device comprises a balloon, preferably an inflatable balloon. The device may further comprise means for inflating the balloon.

The balloon may be substantially in the form of a standard Foley catheters, but a more resilient material is used for the balloon. In case silicone is used as material for the balloon, the silicone may preferably be of a type softer than a shore(A) hardness of 35. Natural rubber, Latex, neoprene or thermoplastic elastomers (as Styrene-Etylene-Butadiene-Coblock-polymers such as Kraton K™) may also be used.

The diameter of the device, when expanded, may preferably be in the range of 30-90 mm, more preferred 50-70 mm and even more preferred 65-55 mm. The design may most preferred enable a size of the expanded balloon to be approx. 60 mm in diameter to ensure a good seal between balloon and bowel wall and the expanded balloon shall not cover the passageway for the enemata fluid, even with an asymmetric deformation of the balloon due to pressure from stool or the bowel wall.

To avoid the mentioned risk of balloon rupture, the balloon material used should preferably be able to withstand an expansion of at least 3 times the prescribed.

Such material can be found among the many polysiloxanes supplied from eg. Dow Corning, NuSil or Rhodia. A preferred embodiment can be made of Silastic® Q7-4720 from Dow Corning.

DESCRIPTION OF THE PREFERRED EMBODIMENTS

The invention is now explained more in detail with reference to the drawings showing preferred embodiments of the invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

A first embodiment of the invention is illustrated in FIG. 1. A catheter-like probe 1 is shown inserted into the bowel system 6 of a user 4 and positioned close to the anal opening 3. A sealing element 2 sealing against the wall 5 of the bowel system 6 is incorporated with the probe 1 and provides for a liquid tight sealing during introduction of irrigation liquid through the cavity 7 and the openings 8 of the probe 1 out into the cavity of the bowel system 6 of the user 4.

FIG. 2a- 2e illustrates sealing devices in a number of preferred alternative shapes as well as it illustrates a number of combinations of sealing device materials and sealing elements.

Figure 2A:
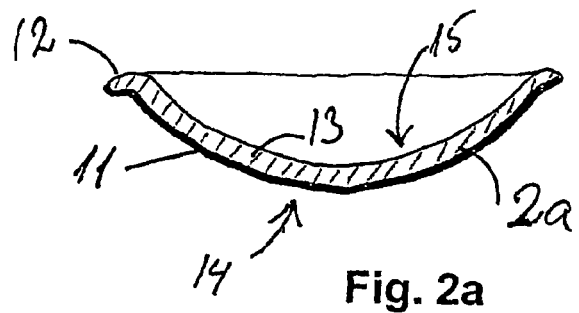
FIG. 2a-2e illustrates the principle of alternative combinations of sealing device materials and sealing elements each constituting a sealing device according to the invention.
Figure 2B:
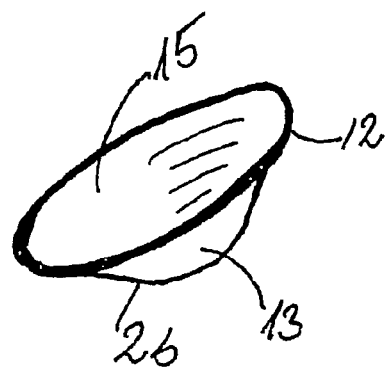
Figure 2C:
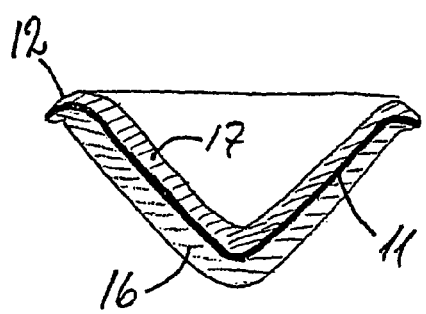

The outer surface 14 of device 2a illustrated in FIG. 2a is provided by a liquid tight foil layer 11, whereas the device 2b illustrated in FIG. 2b is provided with a liquid tight layer on the inner surface 15. As illustrated in FIG. 2c a liquid tight layer 11 is incorporated between two layers of same or different material 16 and 17 facing the outer surface 14 or the inner surface 15 respectively of device 2c.

Figure 2E:
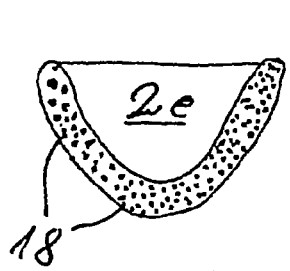
Figure 2D:

FIG. 2d illustrates a device 2d made throughout of a hydrophobic material, while FIG. 2e illustrates a device 2e wherein the sealing element is formed by super-absorbent particles 18 being incorporated in the foam.

Many further combinations of the compressible materials and the liquid tight sealing elements are practicable and may provide for different preferred embodiments for specific uses.

As further illustrated by FIGS. 2a to 2e shape and radial size in relact state, curvature, inclination and thickness of the sealing element as such can vary. Especially a device as illustrated by FIG. 2a, 2b or 2c provides a collar shaped termination 12 of the device providing a curvature somewhat deviating from the curvature of the body part 13 of the sealing device.

Figure 3:
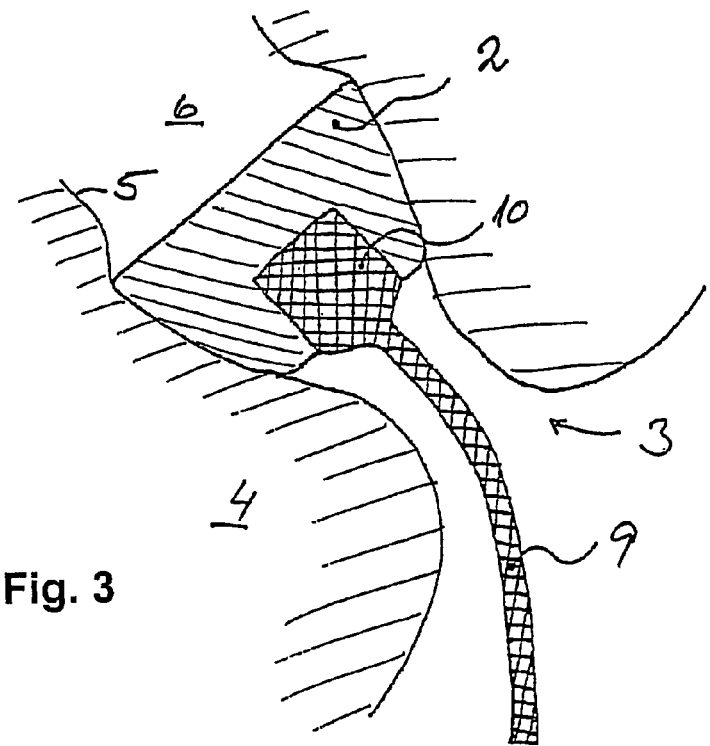
FIG. 3 illustrates a sealing device according to the invention.

FIG. 3 illustrates a sealing device according to the invention positioned close to the anal opening of a user. The sealing device 2 is provided with withdrawal means 9 through an anchor part 10.

Figure 4:
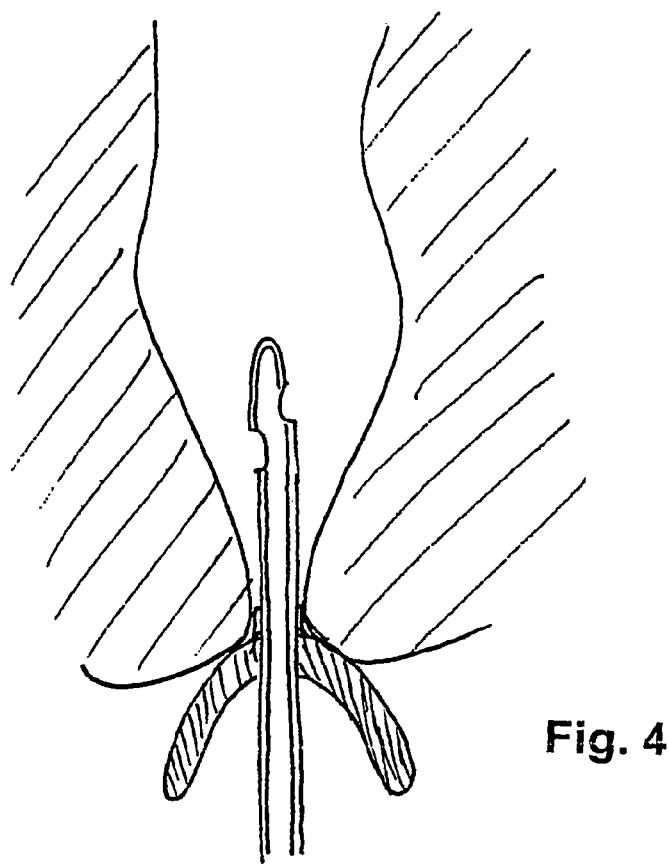
FIG. 4 illustrates a configuration of a dome-shaped sealing device during insertion into the anal canal of a person.

FIG. 4 illustrates the inverted configuration of a dome-shaped sealing device 2 during insertion through the anal opening into the bowel system 6 of a user 4. The sealing device surrounds a catheter like probe 1.

Figure 5A:
FIG. 5 illustrates alternative profiles of the dome-shaped sealing device.
Figure 5B:
Figure 5C:

FIG. 5a-5c illustrates different forms of the outer profile of the sealing element. The radial curve 20 is situated close to the centreline 21 of the device thereby facilitating reversion between two configurations of a dome shaped sealing device.

Methods

In the following and by example a method for use is described in further detail.

EXAMPLE 1

Use of the Device According to the Invention for Anal Irrigation

Preferably anus and at least a first part of the product to be inserted and optionally the anal canal were lubricated with a lubricant such as Vaseline/petrolatum to ease insertion of the probe. The probe was inserted through the anal canal and placed in "ampulla recti", the lower part of the bowel system. A mark or a stop on the probe may be provided to indicates how far the probe it is to be inserted. When inserted the elevated temperature and moisture in the "ampulla recti" will dissolve the PVAH layer surrounding the compressed sealing device and the probe will expand. Now the irrigation media, preferably tab water, was pumped from the reservoir to the bowel (in a typical amount of 0.5-2.5 l, preferably 0.75-1 l). When all the desired water had been pumped into the bowel system the probe was removed immediately or optionally after an additional 1-5 minutes. Evacuation of the bowel will take place over the next maybe 15-45 minutes by reflex action of the bowel system.

An alternative embodiment of a probe including a sealing device according to the invention which is not compressed and wrapped with a PVAH layer as described in the above example was used as follows. Instead of the dome shaped being compressed prior to insertion, it was inserted into the anal canal in inverted configuration. When inserted to a desired depth a slight pull in outward direction was carefully applied to the probe, thereby causing the sealing element to revert to the dome-shaped configuration. The change in configuration was brought about by the pulling force in combination with the resistance applied by the wall of the bowel system to the rim of the sealing device. After use, the probe was carefully removed as described above.

EXAMPLE 2

Determining the Resilience of the Device

An important feature of the device of the present invention is the resilience or softness of the sealing element. The relative resilience of different types of rectal probes was determined in the following way:

A standard tensile strengths apparatus was mounted with two flat plates. The probe was inflated (balloons) or expanded with water (foams) according to manufacturers instructions and inserted between the plates. If the manufacturer did not provide instructions of the size of the probe in the inflated state, inflation to diameter 60 mm was used in the test. The tensile strengths apparatus is activated to compress the balloon/foam 10 mm. The force/mm diagram is recorded and maximum force (N) was achieved. The test was repeated three times for each probe.

Table 1 shows the maximum compression force determined for two embodiments of the invention, a balloon and a foam device, and for different well-known probes in the market.

TABLE 1

| Product | Material | Compr. 1 | Compr. 2 | Compr. 3 | Average |
|---|---|---|---|---|---|
| Balloon device according to the present invention | Neopren | 3.32 | 3.26 | 3.24 | 3.27 |
| Foam device according to the present invention | Polyurethane | 0.47 | 0.43 | 0.40 | 0.43 |
| Radiologic probe (AstraTec) | Latex | 5.54 | 5.50 | 5.46 | 5.50 |
| CardioMed Enema | PE | 21.3 | 20.0 | 19.6 | 20.3 |
| Curity urinary catheter | Silicone | 9.06 | 8.60 | 8.31 | 8.65 |
| OEM Foley catheter | Silicone | 6.50 | 6.36 | 6.29 | 6.38 |
| Sisco Foley catheter | Latex | 14.45 | 14.22 | 14.16 | 14.28 |
| Maersk Medical, soft Foley | Siliconized latex | 14.43 | 14.27 | 14.24 | 14.32 |
| Maersk Medical, hard Foley | Siliconized latex | 14.06 | 13.86 | 13.84 | 13.92 |

As can be seen from the table, the devices according to the invention requires a substantially lower compression force than the probes known in the art, and is thus more resilient.

EXAMPLE 3

Preparation of a Sealing Device

In the following and by example only a method for making a sealing device is described in further detail.

A to-part mould was preheated and parted. The lower part was covered by a 15 µ PU-foil and kept in place e.g. by a rubber band. It is important that the foil is without wrinkles. The upper part of the form was carefully pressed unto the lower part, and a rounded mandrel was entered through the filling opening of the upper part to press and deform the foil. After removal of the mandrel the PU-based foam was formed by introducing the raw materials into the form and blocking the filling opening to stop the formed foam from escaping. The temperature was kept around 50° C. for about 8 minutes, hereafter the form was opened and the device removed for further drying at around 55° C. for approximately 1½ hour.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A sealing device for sealing a body canal of a user, the sealing device comprising:
   an elongated probe defining an irrigation lumen that is provided for administering irrigation liquid through the elongated probe to the body canal, the probe including a distal end portion providing a handle and a proximal end portion defining an opening communicating with the irrigation lumen; and
   a foam sealing element coupled with a central portion of the elongated probe such that the proximal end portion and the opening communicating with the irrigation lumen extend past a proximal end of the foam sealing element, the sealing device including a liquid impermeable member coupled to the foam sealing element to form a fluid barrier to preclude fluid from exiting the body canal when the device is positioned within the body canal, the foam sealing element including a convex outer surface and a concave inner surface that terminate at a collar formed at the proximal end of the foam sealing element, the concave inner surface closer to the proximal end portion of the probe than the convex outer surface is to the proximal end portion of the probe, the collar spaced a distance away from the probe and providing a curved lip that has a curvature different from the convex outer surface and the concave inner surface of the foam sealing element.

2. The sealing device according to claim 1 wherein the foam sealing element includes a hydrophobic foam.

3. The sealing device according to claim 1 wherein the foam sealing element includes absorbent particles incorporated in foam.

4. The sealing device according to claim 1 wherein the liquid impermeable member is coupled to an outer surface of the foam sealing element.

5. The sealing device according to claim 1 wherein the liquid impermeable member is coupled to an inner surface of the foam sealing element.

6. The sealing device according to claim 1 wherein the liquid impermeable member is coupled between an inner surface and an outer surface of the foam sealing element.

7. The sealing device according to claim 1 wherein the foam sealing element is an expandable foam sealing element configured to expand from a first diameter to a second diameter that is larger than the first diameter.

8. The sealing device according to claim 1 wherein the foam sealing element, when inserted into an anus of the user, is compressed a distance of 10 mm in response to a compression force of 4 Newtons or less.

9. The sealing device according to claim 1 wherein the foam sealing element is a U-shaped foam sealing element.

10. The sealing device according to claim 1 wherein the foam sealing element is insertable into an anus of the user and is configured to reduce triggering of anal reflex by providing a pressing force against the anus that is between 0.25-4.0 Newtons.

* * * * *